United States Patent
Reinshagen et al.

(10) Patent No.: US 12,202,774 B2
(45) Date of Patent: Jan. 21, 2025

(54) ALUMINIUM OXIDE CERAMIC MATERIAL

(71) Applicant: Ivoclar Vivadent AG, Schaan (LI)

(72) Inventors: Jörg Reinshagen, Pforzheim (DE); Rick Niebergall, Sersheim (DE)

(73) Assignee: Ivoclar Vivadent AG, Schaan (LI)

(*) Notice: Subject to any disclaimer, the term of this patent is extended or adjusted under 35 U.S.C. 154(b) by 545 days.

(21) Appl. No.: 17/406,133

(22) Filed: Aug. 19, 2021

(65) Prior Publication Data

US 2022/0055948 A1 Feb. 24, 2022

(30) Foreign Application Priority Data

Aug. 21, 2020 (DE) .................. 102020121993.8

(51) Int. Cl.
 *C04B 35/10* (2006.01)
 *C04B 35/626* (2006.01)
 *C04B 35/645* (2006.01)

(52) U.S. Cl.
 CPC .......... *C04B 35/10* (2013.01); *C04B 35/6261* (2013.01); *C04B 35/645* (2013.01); *C04B 2235/3206* (2013.01); *C04B 2235/3224* (2013.01); *C04B 2235/5292* (2013.01); *C04B 2235/549* (2013.01); *C04B 2235/77* (2013.01); *C04B 2235/9661* (2013.01)

(58) Field of Classification Search
 CPC ... C04B 35/10; C04B 35/6261; C04B 35/645; C04B 2235/3206; C04B 2235/3224; C04B 2235/5292; C04B 2235/549; C04B 2235/77; C04B 2235/9661
 See application file for complete search history.

(56) References Cited

U.S. PATENT DOCUMENTS

| | | |
|---|---|---|
| 8,420,006 B2 | 4/2013 | Sakata et al. |
| 8,845,951 B2 | 9/2014 | Maginnis et al. |
| 9,557,114 B2 | 1/2017 | Rohner et al. |
| 10,939,980 B2 | 3/2021 | Fornoff et al. |
| 2006/0073349 A1* | 4/2006 | Aihara .................. C04B 37/005 264/642 |
| 2007/0292597 A1 | 12/2007 | Ritzberger et al. |
| 2010/0221683 A1 | 9/2010 | Franke et al. |
| 2014/0135200 A1 | 5/2014 | Reinshagen |
| 2017/0176103 A1 | 6/2017 | Fornoff et al. |

FOREIGN PATENT DOCUMENTS

| | | | |
|---|---|---|---|
| CN | 106242537 A | | 12/2016 |
| CN | 111072382 A | * | 4/2020 |
| EP | 2101133 A1 | | 9/2009 |
| KR | 101965895 B1 | * | 4/2019 |
| WO | 2007065914 A1 | | 6/2007 |

OTHER PUBLICATIONS

KR101965895B1 machine translation (Year: 2019).*
CN111072382A machine translation (Year: 2020).*
Mendelson, Mel I., "Average Grain Size in Polycrystalline Ceramics," Journal of the American Ceramic Society, vol. 52, No. 8, pp. 443-446, Fairchild Semiconductor Research and Development Laboratory, Palo Alto, California 94304, Aug. 1969.
Zhang Kang, et al., "Effect of MgO/Eu2O3 Co-doping on the Microwave Dielectric Properties of Al2O3 Ceramics," Journal of Inorganic Materials, vol. 30, No. 9, China, Sep. 2015.
Liu, Junchang et al., "Effects of Eu2O3 addition on microstructure, grain-boundary cohesion and wear resistance of high-alumina ceramics," Journal of Alloys and Compounds, 695, pp. 2324-2329, 2017, Elsevier.

* cited by examiner

*Primary Examiner* — James A Fiorito
*Assistant Examiner* — Cameron K Miller
(74) *Attorney, Agent, or Firm* — Ann M. Knab; Thad McMurray

(57) ABSTRACT

An aluminium oxide ceramic material containing the following components:

| component | wt.-% |
|---|---|
| $Al_2O_3$ | 95.0 to 99.989 |
| MgO | 0.001 to 0.1 |
| Eu, calculated as $Eu_2O_3$ | 0.01 to 1.0. |

20 Claims, 4 Drawing Sheets

ALUMINIUM OXIDE CERAMIC MATERIAL

CROSS-REFERENCE TO RELATED APPLICATIONS

This application claims priority to German patent application No. 102020121993.8 filed on Aug. 21, 2020, the disclosure of which is incorporated herein by reference in its entirety.

TECHNICAL FIELD

The present invention relates to an aluminium oxide ceramic material which can be densely sintered within a very short time and which, due to the excellent optical properties thereby obtained, is particularly suitable for the preparation of dental restorations, as well as a process for its preparation. The invention also relates to a process for preparing a sintered aluminium oxide ceramic body using the ceramic material according to the invention and the use of this ceramic material for the preparation of a dental restoration.

BACKGROUND

Ceramic materials such as aluminium oxide ceramics are often used to produce fully anatomical dental restorations. They offer a high degree of clinical safety, are usually metal-free, can also be used for minimally invasive preparations and have a very attractive price compared to other metal-free restorations. The disadvantage, however, is the tedious processing steps that in most cases are required to produce such restorations.

Usually, the restorations are milled or ground from pre-sintered blanks, optionally coloured, densely sintered by thermal treatment and finally optionally further coloured, glazed and/or polished.

In order to provide the mechanical properties of an aluminium oxide ceramic required for industrial or medical applications, hot isostatic post-densification of the sintered material is often carried out. For this the fine-grained aluminium oxide sintered to the closure of the pores is typically post-compressed at 1200° C. to 1300° C. and very high pressures of 1000 to 2000 bar under inert gas, usually argon or nitrogen. A corresponding process is described for example in WO 2007/065914 A1. However, such hot isostatic post-compression requires a great deal of technical effort and is therefore not suitable for chairside treatment directly at the dentist.

Alternatively, aluminium oxide can also be sintered to a transparent state in a hydrogen atmosphere at very high temperatures, typically between 1700° C. and 1900° C. However, the ceramics obtained in this way generally exhibit relatively low strength. In addition, these processes also require a very high technical effort and are therefore also not suitable for chairside treatment directly at the dentist.

Conventional sintering processes for dental ceramics involve slow heating to a maximum temperature at which the oxide ceramic material used is densely sintered. Due to the low heating rate, such a sintering process typically takes significantly more than 4 hours and thus contributes significantly to the unsatisfactory long duration of the production cycle of dental ceramics, especially in chairside treatments.

Approaches to accelerate the sintering process by increasing the heating rate are generally known.

EP 2 098 188 A1 and corresponding US 20090226855, US 20150219397, U.S. Pat. Nos. 9,033,703, and 9,557,114, which US publications and patents are hereby incorporated by reference in their entirety, describe a dental furnace and a process for sintering dental materials, in which the furnace is heated in a first heating period at a rapid heating rate of more than 50 K/min to a pre-sintering temperature of at least 1000° C.

EP 2 101 133 A1 describes a sintering furnace and a method for sintering dental preparations, in which the dental preparations are moved along a sintering path and exposed to different temperatures. High heating rates of 300 K/min or more can be used in a first stage.

WO 2012/057829 A2 and corresponding US 20120267830A1 and U.S. Pat. No. 8,845,951, which US publication and patent are hereby incorporated by reference in their entirety, describe a process for fast sintering of ceramics using electromagnetic induction or a plasma.

WO 2015/091744 A1 and corresponding U.S. Ser. No. 10/939,980 and US 20160317257, which US publication and patent are hereby incorporated by reference in their entirety, describe a method for planning a sintering of a dental prosthesis part, in which a temperature profile for the heat treatment of the dental prosthesis part is automatically determined by a computer depending on certain geometry and material parameters of the dental prosthesis part to be produced. A heating rate between 100 K/min and 400 K/min is used for the sintering of certain prosthesis parts.

WO 2015/121364 A1 and corresponding US 20170176103 which US publication is hereby incorporated by reference in its entirety, describe a sintering furnace for dental components with a heating device that allows a heating rate of at least 200 K/min in the working range.

However, the known approaches to speeding up the sintering process typically lead to a dark, greyish-brown discolouration and in addition to a loss of translucency, so that ceramic materials are obtained whose properties, particularly in terms of optical properties, do not meet the high requirements in particular in the dental field.

Attempts have been made to counteract the discolouration described above by an additional heat treatment following the sintering process. However, this leads to an unacceptable extension of the production cycle, especially for chairside treatments.

SUMMARY

The invention is therefore based on the problem of providing an aluminium oxide ceramic material which can be densely sintered within a very short time, preferably under ambient pressure and ambient atmosphere, without hot isostatic post-compaction, with excellent optical properties, and in particular allows the production of dental restorations with excellent mechanical and in particular optical properties within the scope of a chairside treatment.

BRIEF DESCRIPTION OF THE DRAWINGS

Further advantages, details and features of the invention may be drawn from the following description of a plurality of embodiments with reference to the accompanying drawings, in which.

DETAILED DESCRIPTION

Figure 1:
FIG. 1 shows a visual comparison of test specimens according to the standard sintering program (770 min).

This problem is solved according to the invention by the aluminium oxide ceramic material according to the attached claims. The subject matter of the invention also includes the process for preparing the inventive aluminium oxide ceramic material according to the attached claims, the process for preparing a sintered aluminium oxide ceramic body according to the attached claims, as well as the use of the inventive aluminium oxide ceramic material for preparing a dental restoration according to the attached claims.

The aluminium oxide ceramic material according to the invention is characterized in that it comprises the following components:

| Component | wt.-% |
| --- | --- |
| $Al_2O_3$ | 95.0 to 99.989 |
| MgO | 0.001 to 0.1 |
| Eu, calculated as $Eu_2O_3$ | 0.01 to 1.0. |

Surprisingly, it was found that the aluminium oxide ceramic material according to the invention which comprises europium allows very fast sintering to sintered aluminium oxide ceramic bodies with good mechanical and optical properties. Above all, the aluminium oxide ceramic material according to the invention comprising europium can be densely sintered to dental restorations after appropriate shaping in a very short period of time even under ambient pressure and ambient atmosphere and without the necessity of thermal post-treatment, which restorations nevertheless having very good optical properties and in particular a high translucency and therefore fulfil the high requirements for dental restorations even in terms of aesthetics. This makes it possible to create a densely sintered dental restoration with the desired shape from a blank and to insert it in the mouth of a patient within a single session at the dentist. Such a fast providing of a dental restoration is also called chairside treatment and it is naturally very attractive for the patient. Thus, the aluminium oxide ceramic material according to the invention comprising europium is clearly superior to conventional aluminium oxide ceramic materials, which require very long sintering times, especially to achieve a satisfactory translucency.

It is preferred that the aluminium oxide ceramic material according to the invention comprises at least 96.4, in particular at least 97.4 and preferably at least 98.4 wt.-% $Al_2O_3$. It is particularly preferred that the aluminium oxide ceramic material comprises 96.4 to 99.9, in particular 97.4 to 99.85, preferably 98.4 to 99.8, more preferably 99.4 to 99.75, particularly preferably 99.5 to 99.7 and most preferably 99.55 to 99.65 wt.-% $Al_2O_3$.

Furthermore, an aluminium oxide ceramic material is preferred which comprises 0.005 to 0.09, in particular 0.01 to 0.08, preferably 0.03 to 0.07 and particularly preferably 0.04 to 0.06 wt.-% MgO.

Also preferred is an aluminium oxide ceramic material which comprises 0.05 to 0.9, especially 0.1 to 0.8, preferably 0.2 to 0.7 and particularly preferably 0.3 to 0.6 wt.-% Eu, calculated as $Eu_2O_3$.

Furthermore, an aluminium oxide ceramic material is also preferred which comprises 0.01 to 1.0, in particular 0.05 to 0.5, preferably 0.1 to 0.4 and particularly preferably 0.2 to 0.3 wt.-% Nd, calculated as $Nd_2O_3$.

The aluminium oxide ceramic material according to the invention preferably comprises 0.001 to 2.0, in particular 0.01 to 1.0, preferably 0.05 to 0.8 and particularly preferably 0.1 to 0.5 wt.-% of colouring oxides, the colouring oxides preferably being selected from oxides of Fe, Cr, Mn, Co, Cu, Ag, Er, Pr, Tb, Ce, Ho, Zr and La.

It is also preferred that the aluminium oxide ceramic material comprises no more than 0.5, in particular no more than 0.3, preferably no more than 0.1, particularly preferably no more than 0.05, and most preferably no more than 0.01 wt.-% of other oxides. The term "other oxides" refers to oxides other than those mentioned above, i.e. in particular oxides other than $Al_2O_3$, MgO and oxides of Eu, Nd, Fe, Cr, Mn, Co, Cu, Ag, Er, Pr, Tb, Ce, Ho, Zr and La.

The aluminium oxide ceramic material according to the invention preferably has a number-average grain size in the range of 0.1 to 10.0 µm, in particular 0.5 to 5.0 µm and preferably 0.7 to 2.0 µm. The number-average grain size can be determined in particular by the line-section method according to DIN EN 623-3 or ASTM E 112, wherein the determined value is multiplied by a proportionality constant of 1.56 for conversion to the real number-average grain size in the three-dimensional microstructure according to M. I. Mendelson, J. Am. Ceram. Soc. 1969, 52(8), 443-446.

In a preferred embodiment, the aluminium oxide ceramic material of the invention comprises a europium aluminate crystal phase, wherein the term "europium aluminate" includes in accordance with the invention europium neodymium aluminate. This crystal phase typically comprises rod-shaped or platelet-shaped europium aluminate crystals. Particularly preferably, the aluminium oxide ceramic material comprises rod-shaped europium aluminate crystals, which preferably have an average width of 0.01 to 0.25, particular 0.05 to 0.20, preferably 0.10 to 0.15 and most preferably 0.11 to 0.13 µm and/or an average width to length ratio of 1:1 to 1:10, in particular 1:2 to 1:9, preferably 1:4 to 1:8 and most preferably 1:6 to 1:7.

It is further preferred that the aluminium oxide ceramic material is coloured. According to the invention, this is understood to be a ceramic material including one or more colouring elements. Examples of suitable colouring elements are Fe, Cr, Mn, Co, Cu, Ag, Er, Pr, Tb, Ce, Ho, Zr and La. In particular, the aluminium oxide ceramic material comprises at least two, in particular at least three and preferably at least four layers that differ in colour, and preferably comprises a gradient that exhibits a continuous change in colour.

For the purposes of the present application, the terms 'colour' and 'coloured' refer to the colour, brightness and/or translucency of a material.

"Translucency" is the light transmission of a material, body or layer, i.e. the ratio of transmitted to irradiated light intensity.

Colours can also be characterized by the colour coordinates $L^*$, $a^*$ and $b^*$ in the $L^*a^*b^*$ colour space or by a colour code commonly used in the dental industry. In the $L^*a^*b^*$ colour space, the value $L^*$ describes the brightness of a colour with values from 0 (black) to 100 (white), the value $a^*$ describes the green or red portion of a colour, wherein negative values stand for green and positive values for red, and the value b* describes the blue or yellow portion of a colour, wherein negative values stand for blue and positive values for yellow. Examples of colour codes commonly used in the dental industry are Vitapan Classical® and Vita 3D Master®, both from VITA Zahnfabrik H. Rauter GmbH & Co KG, and Chromascop® from Ivoclar Vivadent AG.

Usually, the determination of the colour coordinates L*, a* and b* is carried out according to DIN 5033 and DIN 6174 and the determination of the translucency according to BS 5612. The corresponding measurements can be carried out in particular with a spectrophotometer of the type CM-3700d (Konica-Minolta). For this purpose, specimens are used for the measurements that have been wet ground with diamond particles (particle size 15-20 µm) on both sides to obtain a final sample thickness of 2.00±0.025 mm or preferably 1.00±0.05 mm. The translucency is calculated from the CR value determined according to BS 5612 using the formula Translucency [%]=100%−CR value [%]

so that a translucency of 0% means completely opaque and a translucency of 100% means completely translucent.

Preferably, the colour or colours of the dental restoration obtained in accordance with the invention are in the range of the shades of natural teeth. Particularly preferably, the aluminium oxide ceramic body obtained in accordance with the invention and in particular the dental restoration obtained in accordance with the invention have an L* value in the range from 50 to 100, especially in the range from 80 to 97, an a* value in the range from −10 to 10, especially in the range from −1 to 5, a b* value in the range from 0 to 50, especially in the range from 1 to 20, and/or a translucency in the range from 35 to 100%, especially in the range from 40 to 99%, preferably in the range from 45 to 98% and most preferably in the range from 50 to 97%.

In another embodiment, the aluminium oxide ceramic material is a non-densely sintered and in particular a pre-sintered aluminium oxide ceramic material. Usually, such an aluminium oxide ceramic material has a relative density in the range of 45 to 90%, in particular in the range of 50 to 80% and preferably in the range of 55 to 70%, each based on the true density of the aluminium oxide ceramic material.

The relative density is the ratio of the apparent density of the ceramic material to the true density of the ceramic material.

The apparent density of the ceramic material can be calculated by the immersion method according to ISO 18754 from the mass of the dry sample ($m_t$), the apparent mass of the sample immersed in an immersion liquid ($m_i$) and the density of the immersion liquid ($\rho_i$) according to the formula $$\rho = \frac{m_t}{m_t - m_i} \times \rho_i$$

Carbon tetrachloride ($CCl_4$) is preferably used as immersion liquid.

The determination of the true density of the aluminium oxide ceramic material is performed by grinding the aluminium oxide ceramic material to a powder with an average particle size of 10 to 30 µm, in particular 20 µm, based on the number of particles, and determining the density of the powder by means of a pycnometer.

The determination of the particle size can be carried out, for example, with the CILAS® Particle Size Analyzer 1064 from Quantachrome GmbH & Co KG using laser diffraction according to ISO 13320 (2009).

The invention also relates to a process for preparing the aluminium oxide ceramic material according to the invention, in which
(a) at least one starting powder comprising aluminium oxide is pressed, in particular at a pressure of 10 to 1300 MPa and preferably 500 to 1000 MPa, to obtain a powder compact, and
(b) optionally, the powder compact is pre-sintered, in particular at a temperature of 400 to 1000° C., preferably 500 to 800 and particularly preferably 600 to 700° C., to obtain a pre-sintered ceramic body,
wherein the starting powder, the powder compact and/or the pre-sintered ceramic body are contacted with a solution comprising a europium salt and optionally a neodymium salt.

In a preferred embodiment of the process according to the invention, the powder compact and/or the pre-sintered ceramic body is infiltrated with a europium salt and, optionally, with a neodymium salt. Suitable infiltration processes are described for example in US 20140135200 A1, which is hereby incorporated by reference in its entirety.

In a further preferred embodiment of the process according to the invention, the starting powder is coated with a europium salt and, optionally, with a neodymium salt. Suitable coating processes are described for example in US 20070292597 A1, which is hereby incorporated by reference in its entirety.

It is particularly preferred to use at least two, in particular at least three and preferably at least four starting powders comprising aluminium oxide, which differ in their colour. The starting powders are arranged one on top of the other in the form of layers and preferably in the form of a gradient which shows a continuous change of colour.

The invention also relates to a process for preparing a sintered aluminium oxide ceramic body, in which the aluminium oxide ceramic material according to the invention is densely sintered at a sintering temperature of 1200 to 1600° C., in particular 1300 to 1550° C. and preferably 1350 to 1500° C. Preferably, sintering is performed in an oxygen-containing atmosphere, especially in air, and in particular at ambient pressure.

In a preferred embodiment of this process, the time for heating the aluminium oxide ceramic material from room temperature to the sintering temperature for dense sintering, the holding at the sintering temperature and the cooling to the final temperature is no more than 150 min, in particular no more than 120 min, preferably no more than 60 min, particularly preferably no more than 40 min and most preferably no more than 20 min. Here, "final temperature" is understood to be a temperature at which the sintered aluminium oxide ceramic body can be taken in the hand, and it is in particular 15 to 80° C., preferably 25 to 60° C. and particularly preferably about 50° C. "Room temperature" is understood to be a temperature of in particular 15 to 30° C., preferably 20 to 25° C. and particularly preferably about 25° C.

The heating rate is in particular more than 50 K/min, preferably more than 100 K/min and particularly preferably more than 200 K/min. The holding time is in particular less than 30 min, preferably less than 20 min and particularly preferred less than 10 min. The cooling rate from the sintering temperature to the final temperature is in particular more than 50 K/min, preferably more than 100 K/min and particularly preferred more than 150 K/min.

Optionally, the dental restoration obtained after dense sintering can be provided with a veneer, polished and/or glazed.

The process according to the invention is suitable for the manufacture of optical and technical components, jewellery and watches, among other things.

The process according to the invention is particularly suitable for the manufacture of dental restorations. In a preferred embodiment, the sintered aluminium oxide ceramic body is—therefore a dental restoration and in particular a bridge, an inlay, an onlay, a crown, an implant, a veneer, a facet, an abutment, a partial crown, a fixed partial denture, an orthodontic appliance, a space maintainer, a tooth replacement appliance, a splint, dentures, a post, teeth, a jacket, a facing, a cylinder, and a connector. The process according to the invention is particularly suitable for the preparation of dental restorations, especially bridges, comprising two or more units. A process is particularly preferred, in which the aluminium oxide ceramic material is given the shape of the dental restoration before dense sintering, in particular by machining and preferably by grinding or milling.

For the preparation of a dental restoration, the aluminium oxide ceramic material according to the invention is preferably used in the form of a blank. The blank can have any shape. In particular, a shape is chosen that allows the blank to be easily machined in conventional dental grinding and milling devices. The blank is preferably in the form of a block, a block with an interface, such as a hole as an implant interface, a disc or a tooth-like preform. It is preferred that the blank also has a holding—device, such as a holding pin, which is formed in one piece with the blank. This is because it eliminates the need for a holder to be attached later by gluing. The holding device is used to hold the blank in a processing device, such as a CAM machine.

The invention also relates to the use of the aluminium oxide ceramic material according to the invention for the preparation of a dental restoration and in particular a bridge, an inlay, an onlay, a crown, an implant, a veneer, a facet or an abutment.

Preferred embodiments of the use are as described above for the process according to the invention.

The invention is explained in more detail below using examples.

EXAMPLES

General Procedure: Sintering Programs
Standard Sintering Program (770 Min):

| Temperature | Duration |
|---|---|
| about 25° C. to 700° C. | 28 min |
| 700° C. to 1350° C. | 217 min |
| 1350° C. to 1425° C. | 75 min |
| Hold at 1425° C. | 60 min |
| 1425° C. to 350° C. | 358 min |
| 350° C. to 300° C. | 17 min |
| 300° C. to about 50° C. | 15 min |

Fast Sintering Program 1 (130 Min):

| Temperature | Duration |
|---|---|
| About 25° C. to 900° C. | 10 min |
| 900° C. to 1470° C. | 38 min |
| Hold at 1470° C. | 60 min |
| 1470° C. to 1100° C. | 7 min |
| 1100° C. to about 50° C. | 15 min |

Fast Sintering Program 2 (36 Min):

| Temperature | Duration |
|---|---|
| about 25° C. to 500° C. | 1.25 min |
| 500° C. to 1300° C. | 2 min |
| 1300° C. to 1390° C. | 0.25 min |
| Hold at 1390° C. | 30 min |
| 1390° C. to 1200° C. | 0.5 min |
| 1200° C. to about 50° C. | 2 min |

Fast Sintering Program 3 (18 Min):

| Temperature | Duration |
|---|---|
| about 25° C. to 500° C. | 1.25 min |
| 500° C. to 1300° C. | 2 min |
| 1300° C. to 1470° C. | 2 min |
| Hold at 1470° C. | 10 min |
| 1470° C. to 1200° C. | 0.75 min |
| 1200° C. to about 50° C. | 2 min |

In all cases, sintering was carried out under ambient pressure and air atmosphere.

Example 1

From a commercially available aluminium oxide powder (TAIMICRON DS-UF-92M, Taimei Chemicals CO., Ltd. Japan) containing 99.95 wt.-% $Al_2O_3$ and 0.05 wt.-% MgO, cylindrical milling blanks with a diameter of 60 mm were produced by uniaxial pressing at a pressure of 530 MPa and subsequent pre-sintering at a temperature of 675° C. for a period of 120 min. Disc-shaped test specimens with a height of about 1.6 to 2.0 mm and a diameter of about 15 to 17 mm were formed from these milling blanks by milling with a milling machine of the PrograMill PM7 type using milling tools of the PrograMill tool yellow 1.0 and 2.5 type (Ivoclar Vivadent AG, Liechten-stein). The test specimens were divided into 3 groups.

The test specimens of group 1 (comparison) were not infiltrated with europium or neodymium.

The test specimens of group 2 (in accordance with the invention) were infiltrated for 10 s with an aqueous solution containing 6 wt.-% of europium nitrate and then dried at 80° C. for 2 h in a drying cabinet. This resulted in test specimens containing 0.37 wt.-% europium, calculated as $Eu_2O_3$.

The test specimens of group 3 (according to the invention) were infiltrated for 10 s with an aqueous solution containing 8 wt.-% europium nitrate and 4 wt.-% neodymium nitrate and then dried at 80° C. for 2 h in a drying cabinet. This resulted in test specimens containing 0.54 wt.-% europium, calculated as $Eu_2O_3$, and 0.26 wt.-% neodymium, calculated as $Nd_2O_3$.

The test specimens from all three groups were densely sintered with the standard sintering program, the fast sintering program 1, the fast sintering program 2 or the fast sintering program 3 according to the general procedure. The test specimens were then polished with a Buehler AutoMet 250 polishing machine (Buehler, ITW Test & Measurement GmbH, Esslingen, Germany) using a contact pressure of 5 N for 12 min each with a 35 µm diamond grinding wheel and then 18 min with a 15 µm diamond suspension on a polishing wheel.

FIG. 1 shows a visual comparison of a test specimen of group 2 (left) and a test specimen of group 1 (right) according to the standard sintering program (770 min).

Figure 2:
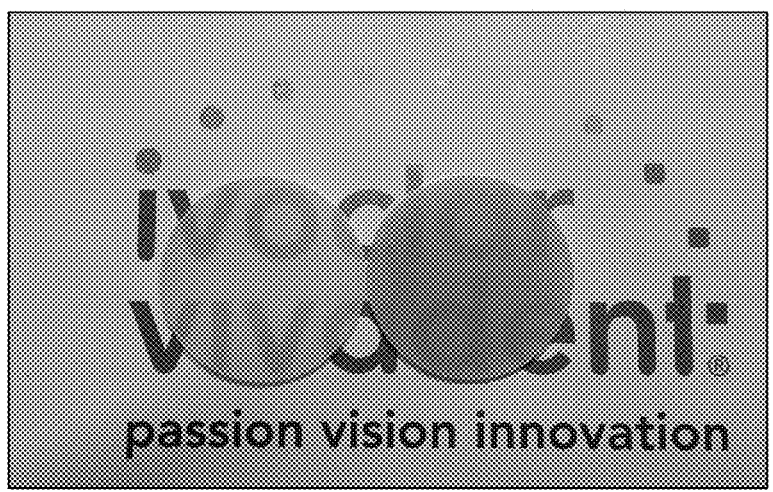
FIG. 2 shows a visual comparison of test specimens after the fast sintering program 1 (130 min).

FIG. 2 shows a visual comparison of a test specimen of group 2 (left) and a test specimen of group 1 (right) after the fast sintering program 1 (130 min).

Figure 3:
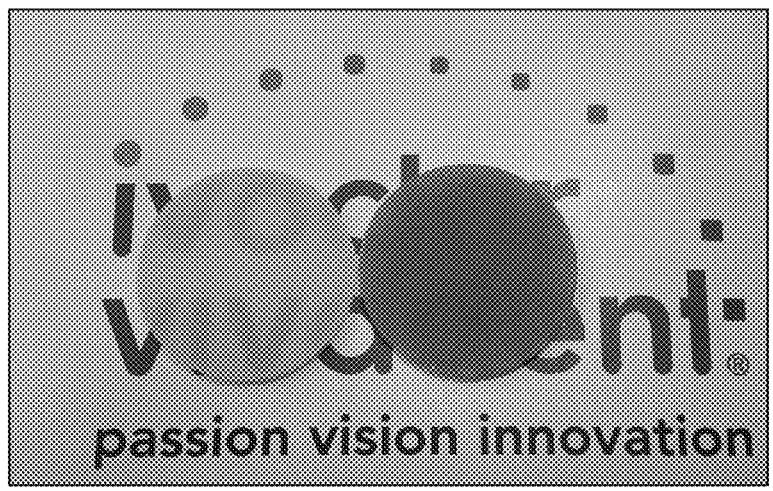
FIG. 3 shows a visual comparison of test specimens after the fast sintering program 2 (36 min).

FIG. 3 shows a visual comparison of a test specimen of group 3 (left) and a test specimen of group 1 (right) after the fast sintering program 2 (36 min).

Figure 4:
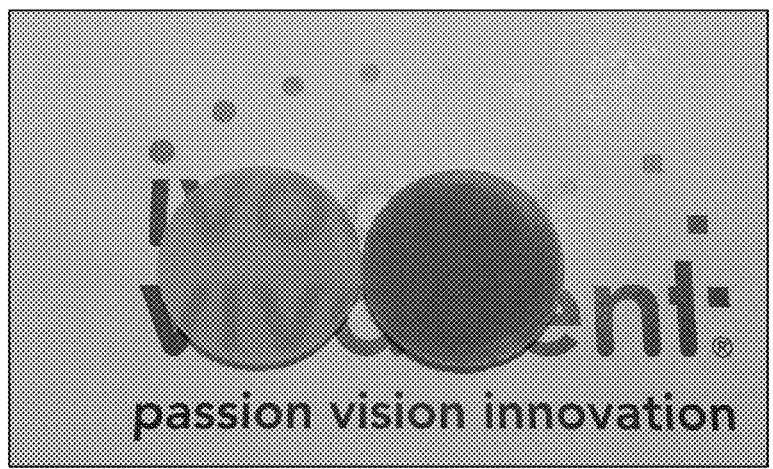
FIG. 4 shows a visual comparison of test specimens of after the fast sintering program 3 (18 min).

FIG. 4 shows a visual comparison of a test specimen of group 2 (left) and a test specimen of group 1 (right) after the fast sintering program 3 (18 min).

The figures clearly show that the test specimens of groups 2 and 3, according to the invention, at least largely avoid an undesired greyish-brown discolouration compared to the test specimens of group 1, and at the same time result in a significantly better translucency.

In addition, the biaxial flexural strength according to DIN EN ISO 6872 and the crack resistance according to ISO 14627:2012 were measured on test specimens that were densely sintered with the standard sintering program or the fast sintering program 1. The results are shown in the following table:

| Group | 1 | 2 | 3 |
|---|---|---|---|
| Eu as $Eu_2O_3$ [weight %] | — | 0.37 | 0.54 |
| Nd as $Nd_2O_3$ [wt %] | — | — | 0.26 |
| biaxial bending strength [MPa] according to standard sintering program | 573 | 555 | 641 |
| biaxial bending strength [MPa] according to fast sintering program 1 | 566 | 617 | |
| Crack resistance [MPa $m^{0.5}$] according to standard sintering program | 3.47 | 3.49 | |
| Crack resistance [MPa $m^{0.5}$] according to fast sintering program 1 | 3.48 | 3.50 | |

Example 2

From a commercially available aluminium oxide powder (TAIMICRON DS-UF-92M, Taimei Chemicals CO., Ltd. Japan) containing 99.95 wt.-% $Al_2O_3$ and 0.05 wt.-% MgO, cylindrical milling blanks with a diameter of 60 mm were produced by uniaxial pressing at a pressure of 950 MPa and subsequent pre-sintering at a temperature of 675° C. for a period of 120 min. From these milling blanks, disc-shaped test specimens with a height of about 1.3 to 1.4 mm and a diameter of about 13 to 14 mm were formed by milling with a milling machine of the PrograMill PM7 type using milling tools of the PrograMill tool yellow 1.0 and 2.5 type (Ivoclar Vivadent AG, Liechten-stein).

The test specimens of group 1 (comparison) were not infiltrated with europium or neodymium.

The test specimens of group 2 (in accordance with the invention) were infiltrated for 10 s with an aqueous solution containing 6 wt.-% of europium nitrate and then dried at 80° C. for 2 h in a drying cabinet. This resulted in test specimens containing 0.36 wt.-% europium, calculated as $Eu_2O_3$.

The test specimens of group 3 (according to the invention) were infiltrated for 10 s with an aqueous solution containing 8 wt.-% europium nitrate and 4 wt.-% neodymium nitrate and then dried at 80° C. for 2 h in a drying cabinet. This resulted in test specimens containing 0.54 wt.-% europium, calculated as $Eu_2O_3$, and 0.26 wt.-% neodymium, calculated as $Nd_2O_3$.

The specimens from all three groups were densely sintered with the fast sintering program 1 in accordance with the general procedure. The test specimens were then polished with a Buehler AutoMet 250 polishing machine (Buehler, ITW Test & Measurement GmbH, Esslingen, Germany) using a contact pressure of 5 N for 12 min each with a 35 µm diamond grinding wheel and then 18 min with a 15 µm diamond suspension on a polishing wheel. After sintering and polishing, the samples had a height of about 1 mm and a diameter of about 10 mm.

Then, the translucency and colour values were measured. The results are shown in the table below:

| Group | 1 | 2 | 3 |
|---|---|---|---|
| Eu as $Eu_2O_3$ [wt.-%] | — | 0.36 | 0.54 |
| Nd as $Nd_2O_3$ [wt.-%] | — | — | 0.26 |
| Translucency [%] | 29.7 | 52.2 | 44.4 |
| L* | 68.15 | 95.79 | 89.06 |
| a* | 5.2 | −1.58 | −0.83 |
| b* | 14.15 | 6.15 | −1.87 |

The results correspond to an average value of 6 test specimens each and are standardized to a specimen thickness of 1.012 mm.

It can be seen that in particular the translucency values of the test specimens of groups 2 and 3 according to the invention are very significantly improved compared to the test specimens of group 1.

Example 3

From a commercially available aluminium oxide powder (TAIMICRON DS-UF-92M, Taimei Chemicals CO., Ltd. Japan) containing 99.95 wt.-% $Al_2O_3$ and 0.05 wt.-% MgO, cylindrical milling blanks with a diameter of 60 mm were produced by uniaxial pressing at a pressure of 510 MPa and subsequent pre-sintering at a temperature of 675° C. for a period of 120 min. From these milling blanks, disc-shaped test specimens with a height of about 1.3 to 1.4 mm and a diameter of about 13 to 14 mm were formed by milling with a milling machine of the PrograMill PM7 type using milling tools of the PrograMill tool yellow 1.0 and 2.5 type (Ivoclar Vivadent AG, Liechten-stein).

The test specimens of group 1 (comparison) were not infiltrated with europium or neodymium.

The test specimens of group 2 (in accordance with the invention) were infiltrated for 10 s with an aqueous solution containing 6 wt.-% of europium nitrate and then dried at 80° C. for 2 h in a drying cabinet. This resulted in test specimens containing 0.36 wt.-% europium, calculated as $Eu_2O_3$.

The test specimens of group 3 (according to the invention) were infiltrated for 10 s with an aqueous solution containing 8 wt.-% europium nitrate and 4 wt.-% neodymium nitrate and then dried at 80° C. for 2 h in a drying cabinet. This resulted in test specimens containing 0.54 wt.-% europium, calculated as $Eu_2O_3$, and 0.26 wt.-% neodymium, calculated as $Nd_2O_3$.

The specimens from all three groups were densely sintered with the fast sintering program 1 in accordance with the general procedure. The test specimens were then polished with a Buehler AutoMet 250 type polishing machine (Buehler, ITW Test & Measurement GmbH, Esslingen, Germany) using a contact pressure of 5 N for 12 min each with a 35 μm diamond grinding wheel and then 18 min with a 15 μm diamond suspension on a polishing wheel. After sintering and polishing, the samples had a height of about 1 mm and a diameter of about 10 mm.

The grain size was then measured. The results are shown in the table below:

| Group | 1 | 2 | 3 |
|---|---|---|---|
| Eu as $Eu_2O_3$ [wt.-%] | — | 0.36 | 0.54 |
| Nd as $Nd_2O_3$ [wt.-%] | — | — | 0.26 |
| Grain size [μm] | 1.657 ± 0.207 | 1.271 ± 0.207 | 1.430 ± 0.239 |

SEM analyses of the specimens were also performed.

Figure 5:
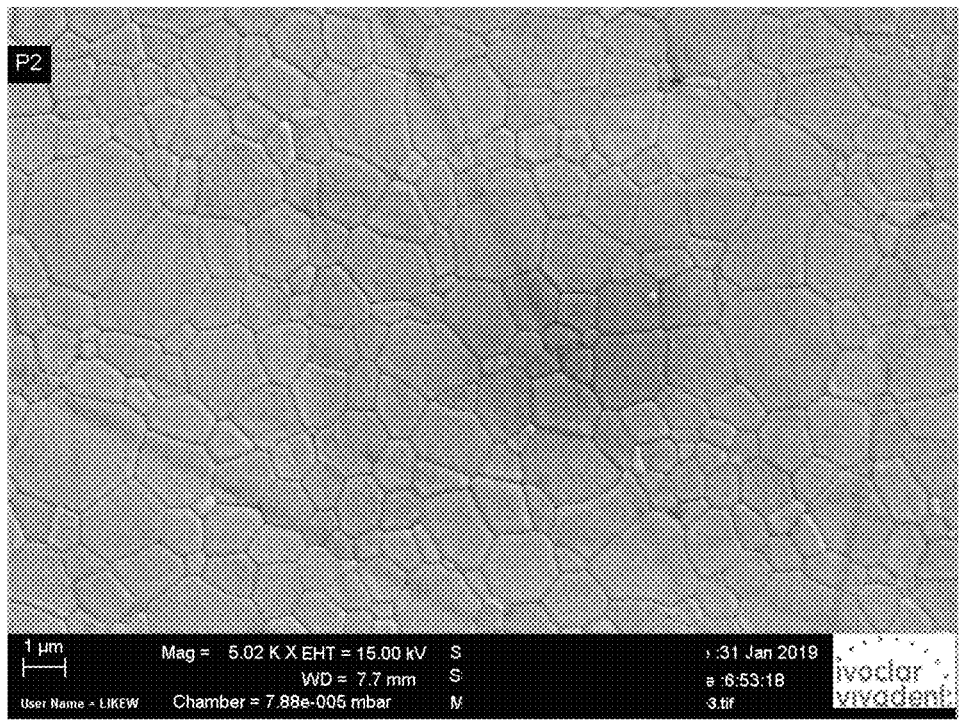
FIG. 5 shows a SEM image of a specimen.

FIG. 5 shows a SEM image of a group 1 specimen.

Figure 6:
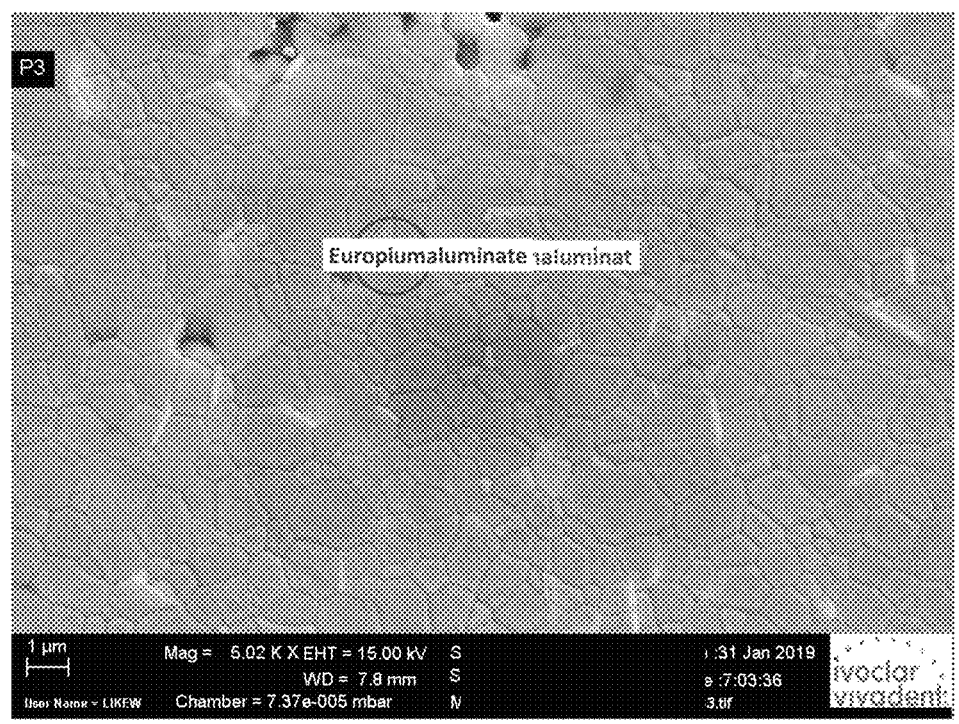
FIG. 6 shows an SEM image of a specimen.
Figure 7:
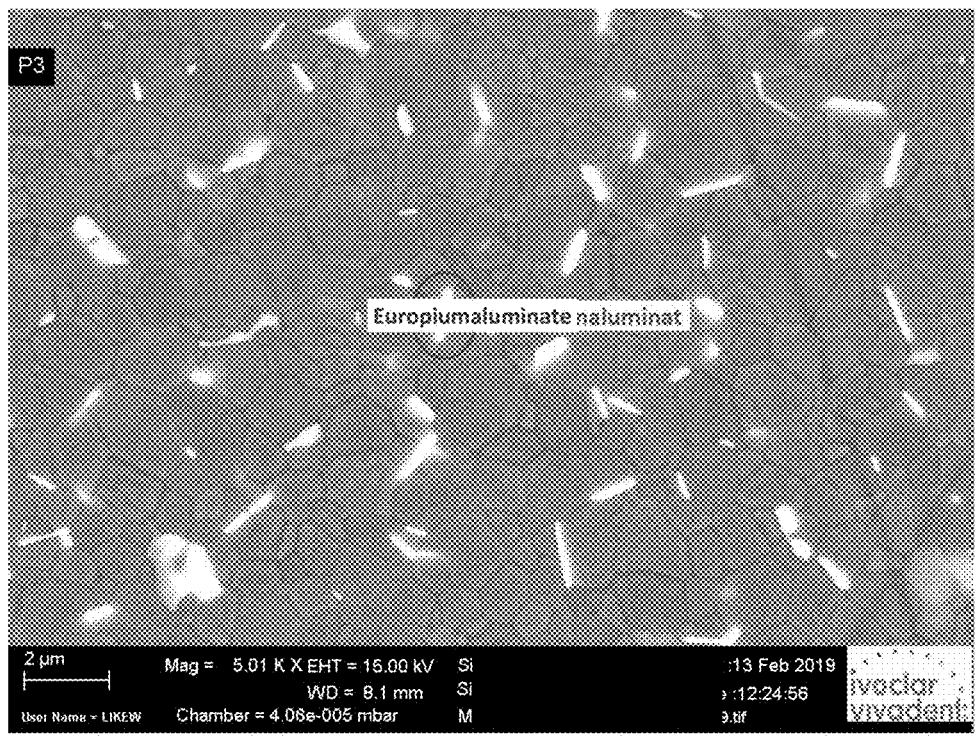
FIG. 7 shows an SEM image of a specimen.

FIGS. 6 and 7 show SEM images of group 2 specimens. Rod-shaped and platelet-shaped europium aluminate crystals are clearly visible, which have a high brightness in the SEM due to the high atomic number of europium.

Figure 8:
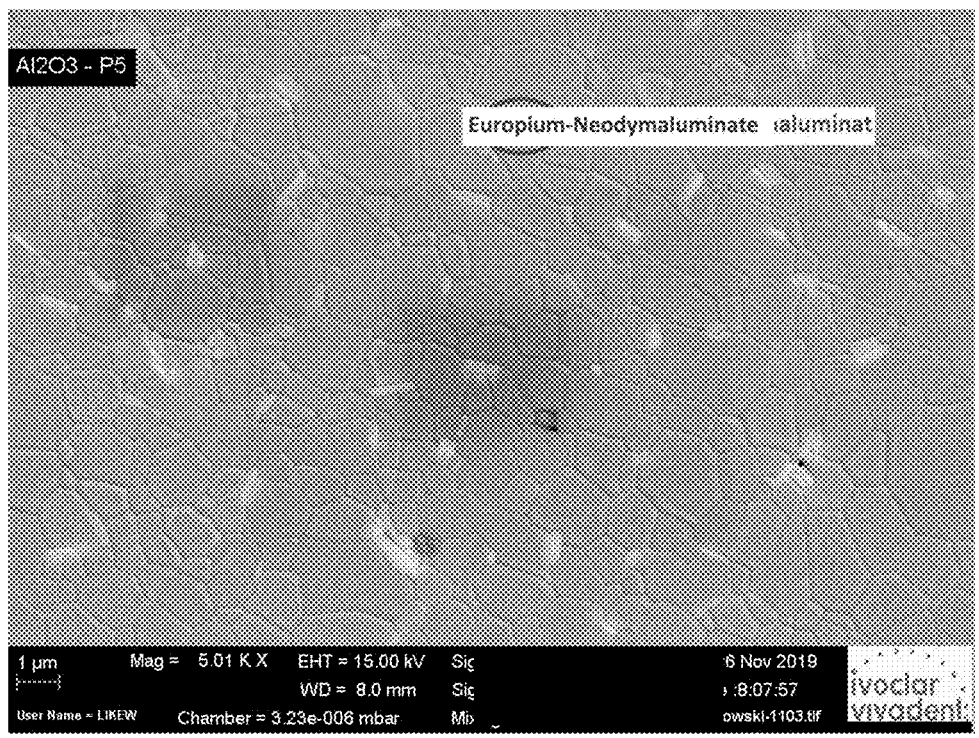
FIG. 8 shows an SEM image of a specimen.

FIG. 8 shows a SEM image of a group 3 specimen. Rod-shaped and platelet-shaped europium-neodymium aluminate crystals are clearly visible, which also have a high brightness in the SEM due to the high atomic numbers of europium and neodymium.

The invention claimed is:

1. An aluminium oxide ceramic material comprising the following components:

| Component | wt.-% |
|---|---|
| $Al_2O_3$ | 95.0 to 99.989 |
| MgO | 0.001 to 0.1 |
| Eu, calculated as $Eu_2O_3$ | 0.01 to 1.0, | which comprises at least two layers differing in colour.

2. The aluminium oxide ceramic material according to claim 1, which comprises at least 96.4 wt.-% $Al_2O_3$.

3. The aluminium oxide ceramic material according to claim 1, which comprises 0.005 to 0.09 wt.-% MgO.

4. The aluminium oxide ceramic material according to claim 1, which comprises 0.05 to 0.9 wt.-% Eu, calculated as $Eu_2O_3$.

5. The aluminium oxide ceramic material according to claim 1, which comprises 0.01 to 1.0 wt.-% Nd, calculated as $Nd_2O_3$.

6. The aluminium oxide ceramic material according to claim 1, which comprises 0.001 to 2.0 wt.-% colouring oxides.

7. The aluminium oxide ceramic material according to claim 1, comprising a gradient which exhibits a continuous change in colour.

8. The aluminium oxide ceramic material according to claim 1, which comprises not more than 0.5 wt.-% of other oxides.

9. An aluminium oxide ceramic material comprising the following components:

| Component | wt.-% |
|---|---|
| $Al_2O_3$ | 95.0 to 99.989 |
| MgO | 0.001 to 0.1 |
| Eu, calculated as $Eu_2O_3$ | 0.01 to 1.0, | which comprises a europium aluminate crystal phase.

10. The aluminium oxide ceramic material according to claim 9, which comprises rod-shaped europium aluminate crystals which have an average width of 0.01 to 0.25 μm and/or an average width to length ratio of 1:1 to 1:10.

11. The aluminium oxide ceramic material according to claim 1, which is not densely sintered.

12. The aluminium oxide ceramic material according to claim 1, which has a relative density in the range of 45 to 90%, based on the true density of the aluminium oxide ceramic material.

13. A process for preparing the aluminium oxide ceramic material according to claim 1, wherein
   (a) at least one starting powder comprising aluminium oxide is pressed, and
   (b) optionally, the powder compact is pre-sintered to obtain a pre-sintered ceramic body,
   wherein the starting powder, the powder compact and/or the pre-sintered ceramic body are contacted with a solution comprising a europium salt and optionally a neodymium salt.

14. The process according to claim 13, in which at least two starting powders comprising aluminium oxide are used which differ in colour, wherein the starting powders are arranged on top of one another in the form of layers and in the form of a gradient which exhibits a continuous change in colour.

15. A process for preparing a sintered aluminium oxide ceramic body, in which the aluminium oxide ceramic material according to claim 1 is densely sintered at a sintering temperature of 1200 to 1600° C.

16. The process according to claim 15, wherein the period of time for heating the aluminium oxide ceramic material from room temperature to the sintering temperature, the holding at the sintering temperature and the cooling to the final temperature is not more than 150 min.

17. The process according to claim 15, wherein the sintered aluminium oxide ceramic body has a translucency in the range from 35 to 100%.

18. The process according to claim 15, wherein the sintered aluminium oxide ceramic body is a dental restoration selected from a bridge, an inlay, an onlay, a crown, an implant, a veneer, a facet, an abutment, a partial crown, a fixed partial denture, an orthodontic appliance, a space maintainer, a tooth replacement appliance, a splint, dentures, a post, teeth, a jacket, a facing, a cylinder, and a connector.

19. The process according to claim 18, wherein the aluminium oxide ceramic material is given the shape of the dental restoration before the dense sintering.

20. A method of using the aluminium oxide ceramic material according to claim 1 for the preparation of a dental restoration selected from a bridge, an inlay, an onlay, a crown, an implant, a veneer, a facet, an abutment, a partial crown, a fixed partial denture, an orthodontic appliance, a space maintainer, a tooth replacement appliance, a splint, dentures, a post, teeth, a jacket, a facing, a cylinder, and a connector.

* * * * *